United States Patent [19]

Nore et al.

[11] Patent Number: 5,530,160
[45] Date of Patent: Jun. 25, 1996

[54] PROCESS FOR THE PREPARATION OF L-ASPARTIC ACID FROM AMMONIUM ASPARTATE

[75] Inventors: Olivier Nore, Beaussais; André Pilot, Celles sur Belle, both of France

[73] Assignee: Rhone-Poulenc Chimie, Courbevoie Cedex, France

[21] Appl. No.: 424,867

[22] Filed: Apr. 17, 1995

[30] Foreign Application Priority Data

Apr. 20, 1994 [FR] France .................................. 94 04714

[51] Int. Cl.$^6$ ................................................ C07C 229/00
[52] U.S. Cl. ................................................ 562/571
[58] Field of Search .............................................. 562/571

[56] References Cited

U.S. PATENT DOCUMENTS 3,933,586  1/1976  Duc ............................................ 195/30
4,560,653  12/1985  Sherwin .................................... 435/109
4,828,993  5/1989  Sridhar ..................................... 435/136

FOREIGN PATENT DOCUMENTS 588674  3/1994  European Pat. Off. ............... 562/571

Primary Examiner—Michael L. Shippen
Attorney, Agent, or Firm—Paul J. Juettner

[57] ABSTRACT

Process for the preparation of L-aspartic acid by treatment of ammonium aspartate using an alcoholic (preferably methanolic or ethanolic) fumaric acid solution according to an added fumaric acid/ammonium aspartate present molar ratio of the order of 0.05 to 0.8 and preferably of the order of 0.1 to 0.65, the said alcoholic solution containing of the order of 1 to 15% and preferably of 3 to 10% of its weight of fumaric acid.

14 Claims, No Drawings

PROCESS FOR THE PREPARATION OF L-ASPARTIC ACID FROM AMMONIUM ASPARTATE

The object of the present invention is a process the preparation of L-aspartic acid by treatment of ammonium aspartate using an alcoholic fumaric acid solution.

It has been proposed, in European Patent Application EP-A-588,674, to prepare L-aspartic acid by treatment of ammonium aspartate using fumaric acid in aqueous medium. This treatment, during which L-aspartic acid crystallizes, can last from approximately 10 minutes to more than one hour, depending on the reaction conditions used. The crystallized L-aspartic acid is subsequently separated by filtration and then washed and dried. The L-aspartic acid yield (with respect to the ammonium aspartate employed) is of the order of 80 mol %.

It has now found that the use of fumaric acid in an alcoholic solution makes it possible to increase the L-aspartic acid yield and additionally does not require a prior crystallization operation on the L-aspartic acid before filtration.

According to the invention, there is provided a process for the preparation of L-aspartic acid by treatment of ammonium aspartate with an alcoholic fumaric acid solution the fumaric acid/ammonium aspartate being present in a molar ratio of the order of 0.05 to 0.8 and preferably of the order of 0.1 to 0.65, the said alcoholic solution containing of the order of 1 to 15% and preferably of 3 to 10% of its weight of fumaric acid.

For good implementation of the process of the invention, the ammonium aspartate is present in the form of an aqueous solution with a concentration of the order of 0.5 to 2.5 mol/liter and preferably of the order of 0.8 to 1.8 mol/liter.

The alcohols which can be used for dissolving the fumaric acid are those which are solvents or partial solvents of fumaric acid but non-solvents of L-aspartic acid. "Solvents or partial solvents" of fumaric acid means those capable of dissolving, under the reaction conditions, at least 5% by weight of fumaric acid. "Non-solvents" of L-aspartic acid means those capable of dissolving, under the reaction conditions, less than 0.5% by weight of L-aspartic acid. Mention may be made, among the preferential alcohols, of methanol, ethanol, and the like.

The treatment of ammonium aspartate using the alcoholic fumaric acid solution can be carried out at a temperature of the order of 20° to 80° C.; a temperature of the order of 30° to 55° C. is generally suitable.

In contrast to the prior process, the L-aspartic acid formed precipitates and crystallizes instantaneously. The latter can be separated by filtration and then washed with water.

The mother liquors containing the residual alcohol, acids and ammonium salts are treated by distillation, in order to recover fumaric acid and the alcohol.

The process which forms the subject of the invention is particularly well suited to the preparation of L-aspartic acid from ammonium aspartate obtained by enzymatic treatment of ammonium fumarate by aspartases or microorganisms which produce aspartases, such as *Pseudomonas fluorescens, Escherichia coli, Aerobacter aerogenes, Bacterium succinium*, Micrococcus sp., *Bacillus subtilis* and *Serratia marcescens*. The ammonium aspartate obtained as a result of the enzymatic treatment is preferably isolated at the end of the enzymatic reaction, for the purpose of the subsequent treatment stage using the alcoholic fumaric acid solution.

The following examples are given by way of illustration.

EXAMPLE 1

Preparation of the fumaric acid+methanol mixture 200 g of 99.8% methanol are introduced into a 500 ml beaker equipped with a magnetic stirring system. This alcohol is brought to 45° C. using a heating plate incorporated in the magnetic stirrer. 10% by weight of fumaric acid (i.e. 20 g) are then introduced while maintaining the temperature at 45° C. 220 g of alcoholic fumaric acid solution are thus obtained.

Precipitation of aspartic acid 300 g of a 1.15 mol/kg aqueous ammonium aspartate solution, which represents 0.345 mol, are introduced into a 500 ml Erlenmeyer flask. This solution is brought to 45° C.

The 220 g of alcoholic fumaric acid solution prepared above, which corresponds to 0.172 mol of fumaric acid and to a fumaric acid/ammonium aspartate molar ratio of 0.5, are then introduced.

The mixture is stirred using a magnetic stirrer. The temperature of the medium, which is 45° C. at the moment of mixing, changes in less than 15 seconds to 50° C., with appearance of a precipitate. After stirring for 15 minutes, the mixture is cooled to 30° C. and then filtered under vacuum (2700 Pa).

The crystals which have been separated by filtration are washed using 40 g of distilled water. After separating the filtrate and drying the wet crystals, the weight of dry crystals obtained is 35 g, which corresponds to an aspartic acid yield of 77%.

By high pressure liquid chromatography, it is observed that the purity of the aspartic acid crystals obtained is 96.1%; their fumaric acid content is 2.25% and their malic acid content is 0.07%.

EXAMPLE 2

Preparation of the fumaric acid+ethanol mixture 200 g of 95% ethanol are introduced into a 500 ml beaker equipped with a magnetic stirring system. This alcohol is brought to 45° C. using a heating plate incorporated in the magnetic stirrer. 7.5% by weight of fumaric acid (i.e. 15 g) are then introduced while maintaining the temperature at 45° C. 215 g of alcoholic fumaric acid solution are thus obtained.

Precipitation of aspartic acid 224 g of a 1.15 mol/kg aqueous ammonium aspartate solution, which represents 0.259 mol, are introduced into a 500 ml Erlenmeyer flask. This solution is brought to 45° C.

The 215 g of alcoholic fumaric acid solution prepared above, which corresponds to 0.129 mol of fumaric acid and to a fumaric acid/ammonium aspartate molar ratio of 0.5, are then introduced.

The mixture is stirred using a magnetic stirrer. The temperature of the medium, which is 45° C. at the moment of mixing, changes in less than 15 seconds to 50° C., with appearance of a precipitate.

After stirring for 5 minutes, the mixture is cooled to 30° C. and then filtered under vacuum (2700 Pa).

The crystals which have been separated by filtration are washed using 108 g of distilled water. After separating and drying, the weight of crystals obtained is 25.7 g, which corresponds to an aspartic acid yield of 75%.

By high pressure liquid chromatography, it is observed that the purity of the aspartic acid crystals obtained is 98.8%; their fumaric acid content is 2.0% and their malic acid content is 0.07%.

We claim:

1. Process for the preparation of L-aspartic acid comprising treating ammonium aspartate using an alcoholic fumaric acid solution according to an added fumaric acid/ammonium aspartate present molar ratio of the order of 0.05 to 0.8, the said alcoholic solution containing of the order of 1 to 15% of its weight of fumaric acid.

2. Process according to claim 1 wherein the added fumaric acid/ammonium aspartate present molar ratio is of the order of 0.1 to 0.65, the said alcoholic solution containing the order of 3 to 10% of its weight of fumaric acid.

3. Process according to claim 1 wherein said ammonium aspartate is present in the form of an aqueous solution with a concentration of the order of 0.5 to 2.5 mol/liter.

4. Process according to claim 3 wherein the ammonium aspartate is present in the form of an aqueous solution with a concentration of the order of 0.8 to 1.8 mol/liter.

5. Process according to claim 1 wherein the alcohol used for dissolving the fumaric acid is a solvent or partial solvent of fumaric acid but is a non-solvent of L-aspartic acid.

6. Process according to claim 5 wherein the alcohol used for dissolving the fumaric acid is methanol or ethanol.

7. Process according to claim 1 wherein the treatment of ammonium aspartate using the alcoholic fumaric acid solution is carried out at a temperature of the order of 20° to 80° C.

8. Process according to claim 7 wherein the treatment of ammonium aspartate using the alcoholic fumaric acid solution is carried out at a temperature of the order of 30° to 55° C.

9. Process according to claim 2 wherein said ammonium aspartate is present in the form of an aqueous solution with a concentration of the order of 0.5 to 2.5 mol/liter.

10. Process according to claim 9 wherein the ammonium aspartate is present in the form of an aqueous solution with a concentration of the order of 0.8 to 1.8 mol/liter.

11. Process according to claim 3 wherein the alcohol used for dissolving the fumaric acid is a solvent or partial solvent of fumaric acid but is a non-solvent of L-aspartic acid.

12. Process according to claim 11 wherein the alcohol used for dissolving the fumaric acid is methanol or ethanol.

13. Process according to claim 3 wherein the treatment of ammonium aspartate using the alcoholic fumaric acid solution is carried out at a temperature of the order of 20° to 80° C.

14. Process according to claim 5 wherein the treatment of ammonium aspartate using the alcoholic fumaric acid solution is carried out at a temperature of the order of 30° to 55° C.

* * * * *